US012728280B2

(12) United States Patent
Choi et al.

(10) Patent No.: US 12,728,280 B2
(45) Date of Patent: Sep. 8, 2026

(54) ORGANIC LIGHT-EMITTING SHORT-TERM VISUAL STIMULATION PLATFORM FOR BRAIN FUNCTION CONTROL

(71) Applicants: KOREA ADVANCED INSTITUTE OF SCIENCE AND TECHNOLOGY, Daejeon (KR); DAEGU GYEONGBUK INSTITUTE OF SCIENCE AND TECHNOLOGY, Daegu (KR)

(72) Inventors: Kyung Cheol Choi, Daejeon (KR); Byeongju Noh, Daejeon (KR); Ja Wook Koo, Daegu (KR); Bitna Joo, Daegu (KR); Ji Yun Lee, Daegu (KR); Ji Eun Lee, Daegu (KR)

(73) Assignees: KOREA ADVANCED INSTITUTE OF SCIENCE AND TECHNOLOGY, Daejeon (KR); DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 152 days.

(21) Appl. No.: 18/835,713

(22) PCT Filed: Feb. 2, 2023

(86) PCT No.: PCT/KR2023/001500
§ 371 (c)(1),
(2) Date: Aug. 2, 2024

(87) PCT Pub. No.: WO2023/149724
PCT Pub. Date: Aug. 10, 2023

(65) Prior Publication Data

US 2025/0144444 A1 May 8, 2025

(30) Foreign Application Priority Data

Feb. 4, 2022 (KR) ........................ 10-2022-0014879

(51) Int. Cl.
*A61N 5/06* (2006.01)

(52) U.S. Cl.
CPC .... *A61N 5/0622* (2013.01); *A61N 2005/0626* (2013.01); *A61N 2005/0648* (2013.01);
(Continued)

(58) Field of Classification Search
CPC .......... A61N 5/0622; A61N 2005/0648; A61N 2005/0653
See application file for complete search history.

(56) References Cited

U.S. PATENT DOCUMENTS 9,984,584 B2 * 5/2018 Walter .................... A61B 5/11
2018/0133431 A1 * 5/2018 Malchano ........... A61N 5/0622
(Continued)

FOREIGN PATENT DOCUMENTS

JP 2007-531062 A 11/2007
JP 2016-043228 A 4/2016
(Continued)

OTHER PUBLICATIONS

Office Action for KR 10-2022-0014879 by Korean Intellectual Property Office dated Sep. 5, 2023.
(Continued)

*Primary Examiner* — Eric D. Bertram
(74) *Attorney, Agent, or Firm* — BROADVIEW IP LAW, PC

(57) ABSTRACT

The present invention relates to an organic light-emitting short-term visual stimulation platform for brain function control. The visual stimulation platform, according to an aspect of the present invention, comprises: an OLED module; a control unit which controls an operation of the OLED module; and a power supply unit which supplies operating power to the OLED module and the control unit, wherein the visual stimulation platform is configured as a wearable
(Continued)

device to project light generated from the OLED module to the eyes of a user under the control by the control unit, and the control unit may include a time setting unit, a brightness setting unit, a frequency setting unit, and a duty ratio setting unit for light generation of the OLED module.

10 Claims, 13 Drawing Sheets

(52) U.S. Cl.
CPC ................ *A61N 2005/0653* (2013.01); *A61N 2005/0663* (2013.01); *A61N 2005/0667* (2013.01)

(56) References Cited

U.S. PATENT DOCUMENTS

| | | | | |
|---|---|---|---|---|
| 2019/0105509 | A1* | 4/2019 | Tsai | A61N 5/0618 |
| 2020/0398021 | A1* | 12/2020 | Garza | A61N 2/006 |
| 2021/0308481 | A1* | 10/2021 | Hayano | A61N 5/0622 |

FOREIGN PATENT DOCUMENTS

| | | | |
|---|---|---|---|
| KR | 20-2017-0002262 | U | 6/2017 |
| KR | 10-2018-0085773 | A | 7/2017 |
| KR | 10-2019-0097032 | A | 8/2019 |
| KR | 10-2020-0070300 | A | 6/2020 |
| KR | 10-2020-0086277 | A | 7/2020 |
| KR | 10-2021-0013014 | A | 2/2021 |
| KR | 10-2021-0040977 | A | 4/2021 |
| WO | 2019/075094 | A1 | 4/2019 |

OTHER PUBLICATIONS

Notice of Allowance for KR 10-2022-0014879 by Korean Intellectual Property Office dated Apr. 18, 2024.

International Search Report for PCT/KR2023/001500 by Korean Intellectual Property Office dated May 9, 2023.

* cited by examiner

100
CONTROL UNIT
(120)
POWER SUPPLY UNIT
(130)
OLED
110
Glass Substrate
ITC
Organics
DMD electrode
111
112
113
114

FIG. 5

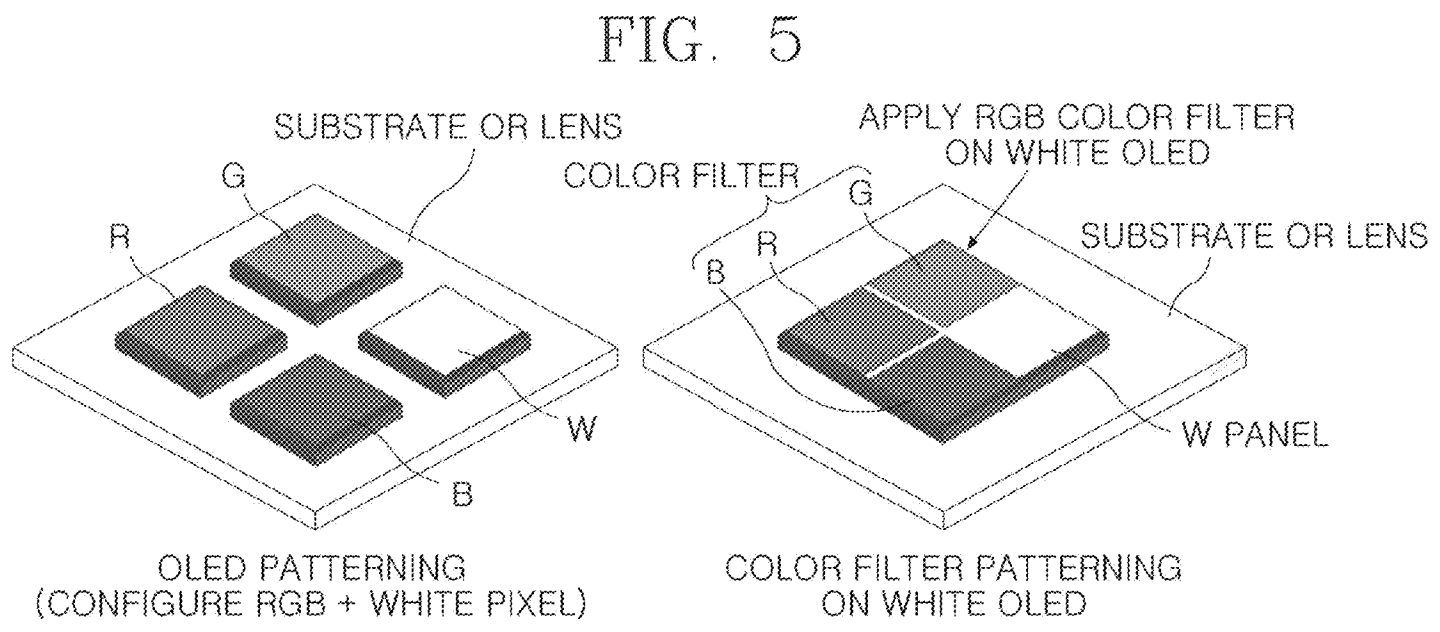

SUBSTRATE OR LENS
G
R
W
B
OLED PATTERNING
(CONFIGURE RGB + WHITE PIXEL)

COLOR FILTER
APPLY RGB COLOR FILTER
ON WHITE OLED
SUBSTRATE OR LENS
W PANEL
G
R
B
COLOR FILTER PATTERNING
ON WHITE OLED

ORGANIC LIGHT-EMITTING SHORT-TERM VISUAL STIMULATION PLATFORM FOR BRAIN FUNCTION CONTROL

CROSS-REFERENCE TO RELATED APPLICATION

This application is a continuation of pending PCT International Application No. PCT/KR2023/001500, filed on Feb. 2, 2023, which claims priority to Korean Patent Application No. 10-2022-0014879 filed on Feb. 4, 2022, the entire contents of which are hereby incorporated by references in its entirety.

TECHNICAL FIELD

The present disclosure relates to a visual stimulation platform for brain function control and, specifically, to a platform adopting a short-term visual stimulation protocol for efficient prevention and recovery of cognitive ability deterioration by using short-term visual stimulation through optimization of light emission uniformity and wavelength of an organic light source of an organic light-emitting diode (OLED).

BACKGROUND ART

A conventional long-term visual stimulation technology has used strong light of a light-emitting diode (LED) to reduce dementia-inducing factors and improve behavior of dementia patients. However, a conventional visual stimulation technology using an LED has a limitation in that it may be difficult to obtain a predetermined effect without repeated stimulation for one hour or more a day for several days. In addition, a conventional visual stimulation technology using an LED has a limitation in that it may be difficult to apply uniform light stimulation to the eyes of a moving subject due to the localized light emission characteristics of the LED and heat generated by concentrated light stimulation of the LED may cause damage to the eye tissue during visual stimulation.

As a related prior document, Patent Application No. 10-2018-7017689 (Nov. 23, 2016) discloses the features of a light-emitting device limited to an optical fiber, invasive stimulation, and application of a chronic stimulation period of at least two days for one hour per day, but there is no technology for wavelength optimization and behavioral improvement.

In addition, Patent Application No. 10-2020-7013288 (Sep. 19, 2018) discloses the features of a light-emitting device limited to a light-emitting diode, and application of a chronic visual stimulation period of seven days, and a visual stimulator characteristic showing a large power consumption of 40 to 80 W. However, the document does not disclose any technology for wavelength optimization and behavioral improvement.

In addition, Patent Application No. 10-2020-7013291 (Oct. 10, 2018) discloses the features of a light-emitting device limited to a light-emitting diode, a stimulation period limited to a minimum of 7 days/22 days/42 days, and a technology for applying an extremely-long-term stimulation of 42 days with respect to a behavior modification stage.

In addition, Patent Application No. 10-2020-7028998 (Nov. 3, 2019) discloses the using of a non-invasive protocol including 40 Hz sensory stray light stimulation and a change in cranial nerve activity through sensory stimulation for 5 minutes, 10 minutes, and 30 minutes for dementia or Alzheimer's disease.

DISCLOSURE OF INVENTION

Technical Problem

In accordance with an aspect of the present disclosure, a short-term visual stimulation platform is provided to effectively prevent deterioration of cognitive ability and achieve quick recovery through behavioral modification with only short-term stimulation while having no restriction in space and time by optimizing light emission uniformity and wavelength of an organic light source of a safe and convenient organic light-emitting diode (OLED) with respect to visual stimulation for controlling a brain function of a subject with a brain lesion disorder, such as sleep disorders, dementia, and Alzheimer's disease.

Solution to Problem

To sum up the features of the present disclosure, a visual stimulation platform according to an aspect of the present disclosure to achieve the aforementioned purpose may include an OLED module, a control unit which controls an operation of the OLED module, and a power supply unit which supplies operating power to the OLED module and the control unit, wherein the visual stimulation platform is configured as a wearable device to project light generated from the OLED module to the eyes of a user under the control by the control unit, and the control unit may include a time setting unit, a brightness setting unit, a frequency setting unit, and a duty ratio setting unit for light generation of the OLED module.

The OLED module may include a white light OLED panel and a color filter configured to transmit light of a specific wavelength range, or may emit light of a wavelength range according to an EML design thereof without a color filter.

The OLED module may adopt a micro-cavity method that emits light of a specific wavelength range.

The OLED module may include multiple OLED areas having different emission colors, and the control unit may further include a wavelength setting unit configured to selectively operate one or more of the multiple OLED areas and control to generate corresponding light.

The multiple OLED areas may include one white light OLED panel and a color filter configured to transmit light of different wavelength ranges, or may include areas configured to emit light of different wavelength ranges according to an EML design thereof without a color filter.

It is preferable for the OLED module to generate light in a W (white), R (red), or G (green) wavelength range through the wavelength setting unit.

The time setting unit may control light generation in a range of 30 minutes to 2 hours, the brightness setting unit may control light generation in a range of 10 to 1000 lux, the frequency setting unit may control continuous light generation driving or light generation on/off frequency driving of 1 to 100 Hz, and the duty ratio setting unit may control a duty ratio of 10 to 90% of the frequency driving.

The visual stimulation platform may include a wearable item (e.g., glasses, a patch, a lens, etc.) configured to be close to the user's eyes and enable the visual stimulation when worn by the user.

The visual stimulation platform may be additionally provided to a wearable product so as to configure a wearable item (e.g., a hat, a hair band, a head-up display (HUD), or the like) to be close to the user's eyes and enable the visual stimulation when worn by the user.

The OLED module may include an anode electrode and a cathode electrode which are made of a semi-permeable film or a transparent conductive film and operate in a first mode in which light generated from the OLED module stimulates the user's eye and a second mode in which when the light generation of the OLED module is turned off, a field of view of the user wearing the visual stimulation platform is secured through the OLED module.

In case of operation in the second mode, while the light generation on/off frequency driving set through the frequency setting unit is performed, brightness of light while the OLED module is turned on, which is set through the brightness setting unit may have a smaller value in the second mode than in the first mode, and in the same frequency set through the frequency setting unit, a duty ratio set through the duty ratio setting unit may have a smaller value in the second mode than in the first mode.

In case of operation in one selected from among the first mode and the second mode, a time set through the time setting unit may have a greater value in the second mode than in the first mode.

Advantageous Effects of Invention

According to the short-term visual stimulation platform of the present disclosure, it is possible to emit light to a wide emission range by using a safe and convenient organic light source of an OLED so as to effectively prevent deterioration of cognitive ability and achieve quick recover through behavioral modification with respect to visual stimulation for controlling a brain function of a subject with a brain lesion disorder, such as sleep disorders, dementia, and Alzheimer's disease, consume low power due to short-term visual stimulation, and significantly lower a side effect, such as possibility of tissue destruction due to local light stimulation so that effective visual stimulation may be achieved. Furthermore, multicolor organic light emission is possible through a frequency adjustment technology so that it is possible to provide a light wavelength optimized to achieve effective treatment for cognitive ability improvement and various neurological diseases such as a sleep disorder.

Furthermore, according to the short-term visual stimulation platform of the present disclosure, it is possible to provide stable visual stimulation even to a moving subject by using a uniform and extensive light emission characteristic of the OLED through the visual stimulation platform (e.g., glasses) on which multicolor OLEDs are deposited, and provide a light wavelength optimized for a neurological disease requiring treatment by using a wavelength adjustment technology.

For example, the use of OLED as a light source may enable uniform light emission with respect to a target visual stimulation range and selection of a wavelength optimized for non-invasive visual stimulation so as to obtain an effect in treatment for recovering a cognitive ability of the subject with a low power consumption of about 1 to 10 W even for short-term (e.g., about 1 hour) visual stimulation. In addition, a light-emitting layer of the OLED, which is a light source, may configure a multicolor light emitting source by using white light, a color filter, a microcavity, patterning, and the like. Therefore, even within one visual stimulation platform, light having various wavelengths may be emitted and thus it is possible to select a customized light source wavelength not only for cognitive ability improvement but also for various neurological diseases, such as a sleep disorder. In addition, the OLED light source is advantageous in that the OLED light source has excellent flexibility and stretchability compared to other light sources, may be applied to various curved surfaces and materials, and thus may be unrestrictedly applied to various platforms, such as glasses, hats, augmented reality/virtual reality (AR/VR) devices, head-up displays (HUD), patches, hair bands, and lenses. In addition, stable visual stimulation is possible in that light reaching the eyeball may be designed to be uniform according to a curvature of a substrate.

BRIEF DESCRIPTION OF DRAWINGS

In order to help understanding of the present disclosure, the accompanying drawings which are included as a portion of the detailed description provide embodiments of the present disclosure and are provided to describe the technical features of the present disclosure together with the detailed description.

FIG. 5 is a view illustrating a color light emission method in which a color filter is applied to a white light panel and a color light emission method using multiple OLED areas of the OLED module in FIG. 1.

BEST MODE FOR CARRYING OUT THE INVENTION

Figure 1:
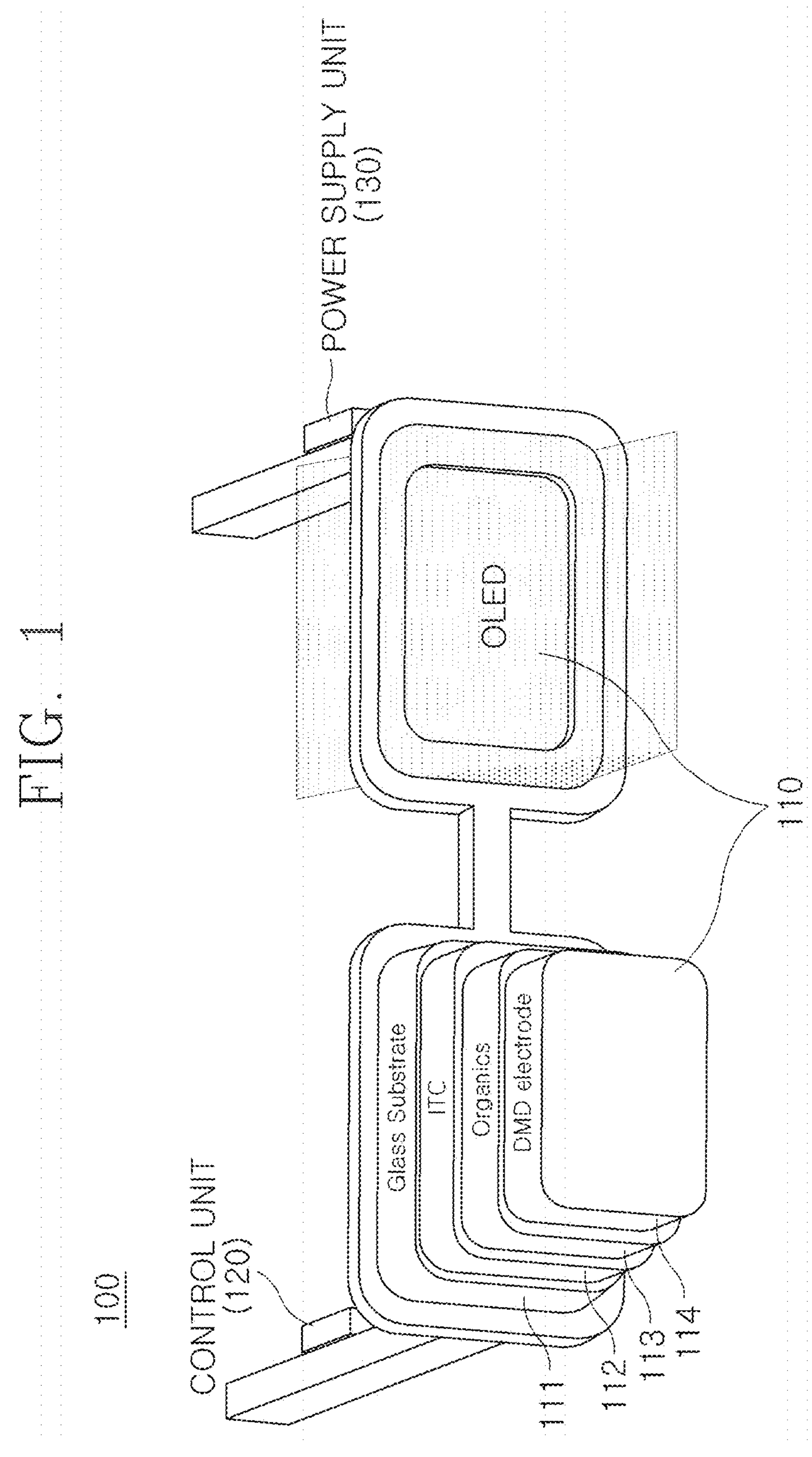
FIG. 1 is a view illustrating a visual stimulation platform according to an embodiment of the disclosure.

Hereinafter, the present disclosure will be described in detail with reference to the accompanying drawings. Here, the same components in each drawing are represented by the same reference numerals as much as possible. In addition, a detailed description of functions and/or configurations that are already known will be omitted. In a description below, a portion necessary for understanding operations according to various embodiments will be mainly described, and a description of an element that may obscure the gist of the description will be omitted. Furthermore, some components in the drawings may be exaggerated, omitted, or schematically illustrated. A size of each component does not entirely reflect an actual size, and therefore, contents described herein are not limited by a relative size or spacing of the components drawn in each drawing.

In describing embodiments of the present disclosure, if it is determined that a detailed description of the known technology related to the present disclosure may unnecessarily obscure the subject matter of the present disclosure, the detailed description will be omitted. The terms which will be described below are terms defined in consideration of the functions in the disclosure, and may be different according to users, intentions of the users, or customs. Therefore, the definitions of the terms should be made based on the contents throughout the specification. Terms used in the detailed description are only for describing the embodiments of the present disclosure, and should not be limiting. Unless explicitly stated otherwise, a singular form of an expression includes the meaning of a plural form. In this description, expressions such as "comprising" or "including" are intended to indicate certain features, numbers, steps, operations, elements, parts or combinations thereof, and one or more than those described and it should not be construed to exclude the existence or possibility of any other characteristic, number, step, operation, element, or part or combination thereof.

In addition, terms such as "first" and "second" may be used to describe various components, but the components are not limited by the terms, and the terms are used only for the purpose of distinguishing one component from another.

FIG. 1 is a view illustrating a visual stimulation platform 100 according to an embodiment of the disclosure.

Referring to FIG. 1, the visual stimulation plat form 100 for brain function control of a user according to an embodiment of the present disclosure includes an OLED module 110, a control unit 120 which controls an operation of the OLED module 110, and a power supply unit 130 which supplies operating power to the OLED module 110 and the control unit 120. The power supply unit 130 may have a form which a battery is mounted or a form in which power is supplied from a power supply device having an AC/DC converter built therein through a power input terminal.

FIG. 1 illustrates an embodiment in which the visual stimulation platform 100 is configured in a form of glasses. In addition, the visual stimulation platform 100 of the present disclosure may be realized in various forms configured to be wearable to project light generated from the OLED module 110 to the user's eye under control of the control unit 120.

Figure 10:
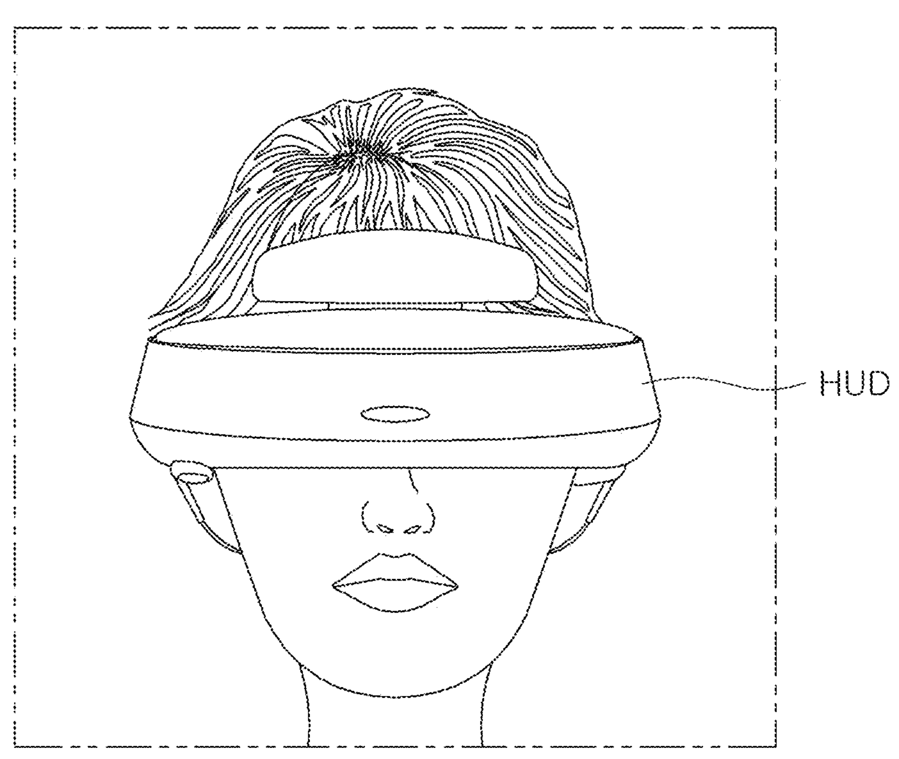
FIG. 10 is a view illustrating an example of a head up display (HUD) as an AR/VR device.

For example, the visual stimulation platform 100 may adopt the configuration described above to be realized in a form of a wearable item (e.g., glasses, a patch, a lens, etc.) configured to be close to the user's eyes and enable the visual stimulation when worn by the user. Alternatively, the visual stimulation platform 100 may configure a wearable item through additional disposition to a wearable product. That is, the configuration of the visual stimulation platform 100 described above may be realized through additional disposition to a wearable product, such as an augmented reality/virtual reality (AR/VR) device (see FIG. 10) including a hat, a hair band, or a head-up display (HUD) so as to be close to the user's eyes to provide visual stimulation when worn by the user.

As such, the visual stimulation platform 100 of the present disclosure may be realized as a wearable item such as glasses, a patch, or a lens, or may be additionally configured in a wearable product such as an AR/VR device. Particularly, in case that the platform is realized in a form of glasses, as shown in the drawing, the visual stimulation platform 100 may include a transparent portion (e.g., a shape similar to a lens portion of glasses) for both eyes, in which the OLED module 110 is installed, and a frame configured to support the OLED module 110 in the form of glasses, wherein both ends of the frame may have a portion configured to be worn by the user's ears (e.g., a shape similar to a frame of glasses and a portion worn by the ear). In this case, components required for an operation of the OLED module 110, such as the control unit 120 and the power supply unit 130, may be provided on an external side of the frame or properly provided in an internal space of the frame.

Figure 2:
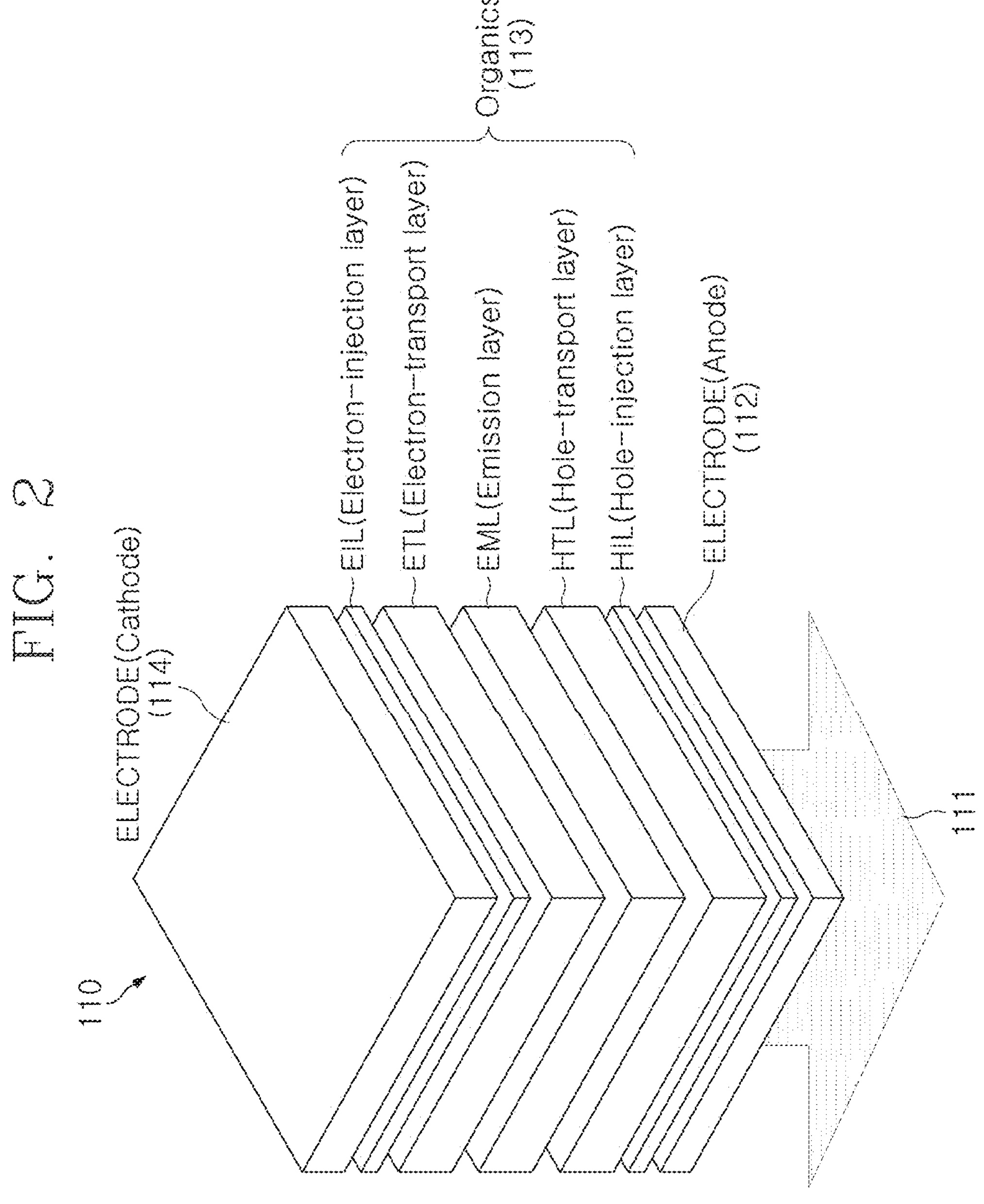
FIG. 2 is a view illustrating a schematic structure of an OLED module in FIG. 1.

FIG. 2 is a view illustrating a schematic structure of an OLED module 110 in FIG. 1.

Referring to FIG. 2, the OLED module 110 includes an anode electrode 112, an organic film layer 113, and a cathode electrode 114 stacked on a transparent substrate 111, such as glass, plastic, quartz, and a lens to generate (emit) light. The organic film layer 113 includes layers such as a hole-injection layer (HIL), a hole-transport layer (HTL), an emission layer (EML), an electron-transport layer (ETL), and an electron-injection layer (EIL).

Power of the power supply unit 130 may be applied between the anode electrode 112 and the cathode electrode 114 so as to output light emitted in colors such as R (Red), G (Green), B (Blue), and W (White) according to a proper design of the organic film layer 113, especially, the emission layer (EML). The cathode electrode 114 may include a reflective film or a semi-transmissive film and a multi-layer thin film structure, such as a dielectric-metal-dielectric (DMD) structure may be used therefor. Light emitted from the organic layer 113 may be released through the anode electrode 112 including a semi-transmissive layer or a transparent conductive layer such as indium Tin oxide (ITO). The OLED module 110 may adopt a micro-cavity method that emits light of a predetermined wavelength range. For example, the micro-cavity method may use an interference effect between light generated inside the organic film layer 113 to emit light amplified at a predetermined wavelength to the outside, and may be realized by configuring the cathode electrode 114 with a semi-transmissive film and properly designing a thickness of the organic film layer 113. The operation of the OLED module 110 and the operation of the micro-cavity method are well known, and thus a detailed description thereof will be omitted.

Figure 3:
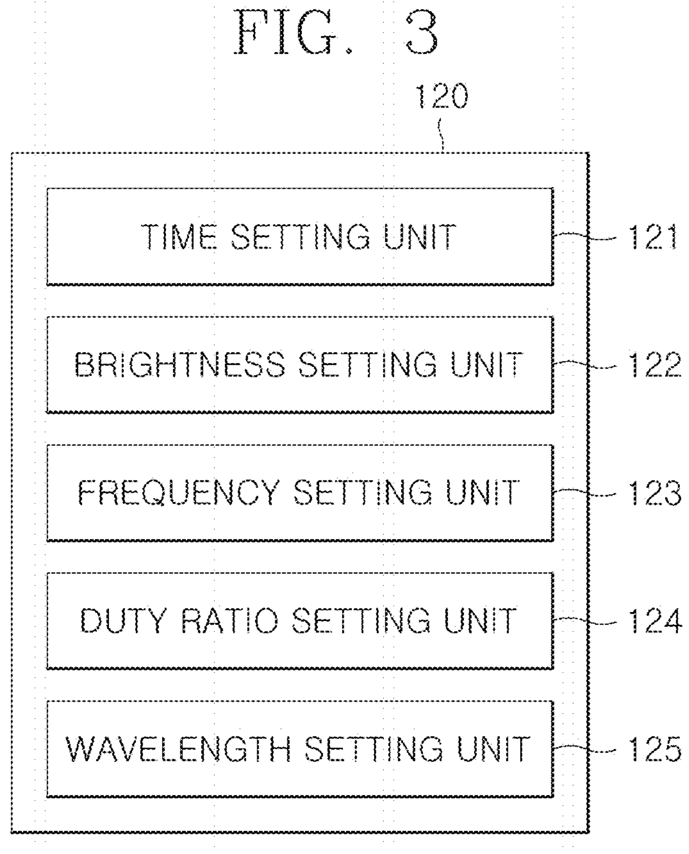
FIG. 3 is a specific block view illustrating a control unit in FIG. 1.

FIG. 3 is a specific block view illustrating a control unit 120 in FIG. 1.

Referring to FIG. 3, the control unit 120 may include a time setting unit 121, a brightness setting unit 122, a frequency setting unit 123, and a duty ratio setting unit 124 for light generation of the OLED module 110 and may further include a wavelength setting unit 125.

Figure 4:
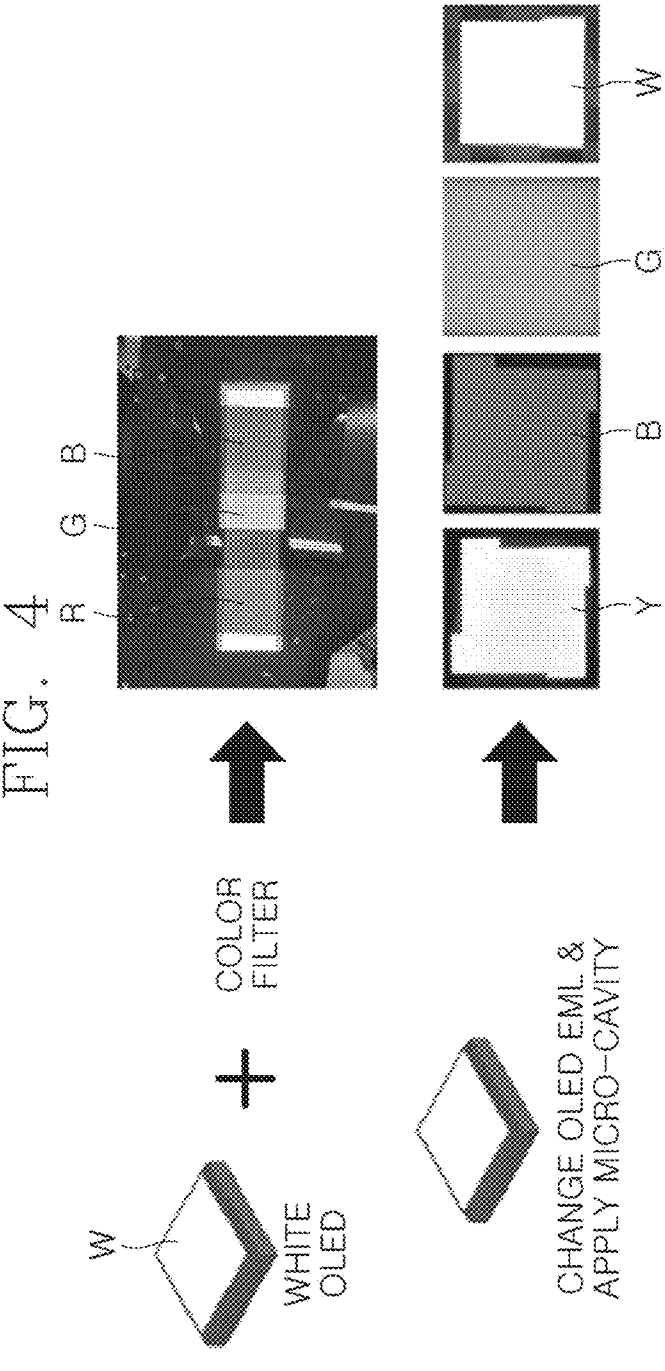
FIG. 4 is a view illustrating a color light emission method of a monochromatic OLED panel of the OLED module in FIG. 1.

The OLED module 110 may correspond to a module emitting light in a predetermined color as shown in FIG. 4 and a proper means, such as a connection means, may be included to allow replacement of another module configured to generate light in a required wavelength range (e.g., 400 to 1100 nm) with respect to the visual stimulation platform 100.

In addition, the OLED module 110 may include a module including multiple OLED areas having different emission colors as shown in FIG. 5, and the wavelength setting unit 125 of the control unit 120 may control one or more of the multiple OLED areas to be selectively operated to generate light in a corresponding wavelength range (e.g., 400 to 1100 nm).

With reference to FIGS. 4 and 5, a method for configuring a monochromatic OLED and the multiple OLED areas of the OLED module 110 will be described in more detail.

FIG. 4 is a view illustrating a color light emission method of a monochromatic OLED panel of the OLED module 110 in FIG. 1.

As shown in FIG. 4, the OLED module 110 may be realized to include, on a white light W OLED panel, color filters for colors generated by a combination of one or more of R (red), G (green), and B (blue) to transmit light of a predetermine wavelength, that is, to output light in a predetermined color. In addition, in order to output light in a predetermined color, the OLED module 110 may be realized to emit light (e.g., R (red), G (green), B (blue), Y (yellow), W (white), and the like) in a wavelength range according to an EML (layer) design thereof as described above without a color filter. In this case, the micro-cavity method may be applied.

As such, the white light W OLED panel or the OLED panels of R (red), G (green), B (blue), Y (yellow), and the like may be configured to have a structure in units of predetermined repeated pixel sizes as shown in FIG. 2.

FIG. 5 is a view illustrating a color light emission method in which a color filter is applied to a white light panel and a color light emission method using multiple OLED areas of the OLED module 110 in FIG. 1.

As shown in FIG. 5, the multiple OLED areas of the OLED module 110 may include areas (R, G, B, W, and the like) emitting light in different wavelengths according to the EML (layer) design thereof without a color filter on the substrate 111, such as a lens (the left part of the drawing). Areas such as R, G, B, and W may be configured to be repeated in a predetermined pixel size (e.g., tens to hundreds of micrometers), or each area may be also configured to be provided only once on the OLED module 110 in a predetermined size (e.g., several centimeters horizontally and vertically).

Alternatively, the multiple OLED areas of the OLED module 110 may include color filters (R, G, B, and the like) for transmitting light of different wavelengths on one white light OLED panel (the right part of the drawing). Areas such as R, G, B, and W may be configured to be repeated in a predetermined pixel size (e.g., tens to hundreds of micrometers horizontally and vertically) depending on the color filter design, or each area may be also configured to be provided only once on the OLED module 110 in a predetermined size (e.g., several centimeters horizontally and vertically).

The time setting unit 121, the brightness setting unit 122, the frequency setting unit 123, and the duty ratio setting unit 124 included in the control unit 120 shown in FIGS. 1 and 3 will described in more detail. Components such as the time setting unit 121, the brightness setting unit 122, the frequency setting unit 123, and the duty ratio setting unit 124 of the control unit 120 may be realized in hardware such as a semiconductor processor, software such as an application program, or a combination thereof. In addition, the above components of the control unit 120 in charge of overall control may be realized as sub-components in which each component is separated into multiple functions, or may be realized as an integrated configuration in which functions of two or more components are combined. Furthermore, some functions of the control unit 120 may be realized in a form of separate components as other units. Although not shown, the control unit 120 may include a user interface such as a display, a touch screen, or a button to configure data necessary for an operation of the visual stimulation platform 100, and may include a memory to store the data or configuration information.

The time setting unit 121 may control light generation of the OLED module 110 in a range of 30 minutes to 2 hours. To this end, the user may select and input a predetermined time (e.g., 1 hour) through the user interface so that the time setting unit 121 may control the OLED module 110 to emit light for the selected time using a timer or the like.

The brightness setting unit 122 may control light generation of the OLED module 110 in a range of 10 to 1000 lux. To this end, the user may select and input a predetermined brightness value (e.g., 100 lux) through the user interface, so that the brightness setting unit 122 may control a signal value (e.g., a voltage or current between electrodes and the like) input to the OLED module 110 to cause the OLED module 110 to generate light with corresponding brightness.

The frequency setting unit 123 may control driving of the OLED module 110 so that the OLED module 110 continuously generates light with the corresponding brightness for the set time as above. Furthermore, the frequency setting unit 123 may control driving of the OLED module 110 so that the OLED module 110 turns on/off light generation with a frequency of 1 to 100 Hz. When the frequency setting unit 123 drives the OLED module 110 to be turned on or off at a predetermined frequency, the duty ratio setting unit 124 may control a duty ratio of 10 to 90% of the frequency driving.

To this end, the user may select and input a continuous light generation mode or an on/off mode having a predetermined frequency value (e.g., 50 Hz) and a duty ratio (e.g., 40%) through the user interface, so that the frequency setting unit 123 may control the OLED module 110 to generate light in a corresponding mode.

As described above, the OLED module 110 may correspond to a module emitting light in a predetermined color as shown in FIG. 4 and a proper means, such as a connection means, may be included to allow replacement of another module configured to generate light in a required wavelength range (e.g., 400 to 1100 nm) with respect to the visual stimulation platform 100.

Furthermore, the OLED module 110 may include a module including multiple OLED areas having different emission colors as shown in FIG. 5, and the wavelength setting unit 125 of the control unit 120 may control one or more of the multiple OLED areas to be selectively operated to generate light in a corresponding wavelength range (e.g., 400 to 1100 nm). To this end, the user may select an input value through the user interface to emit light of a desired wavelength, so that the wavelength setting unit 125 may control the signal values input to the OLED module 110 so as to control one or more of the multiple OLED areas of the OLED module 110, which emit light of different wavelengths, to be selectively operated to generate light of the corresponding wavelength.

Hereinafter, a description will be given of the results of verifying the usefulness of the present disclosure by applying the visual stimulation platform 100 to a mouse and acquiring a result (alternation triplet) of a Y-maze test and a result (discrimination rate) of a novel object recognition (NOR) test based on short-term visual stimulation from the OLED module 110.

Figure 6:
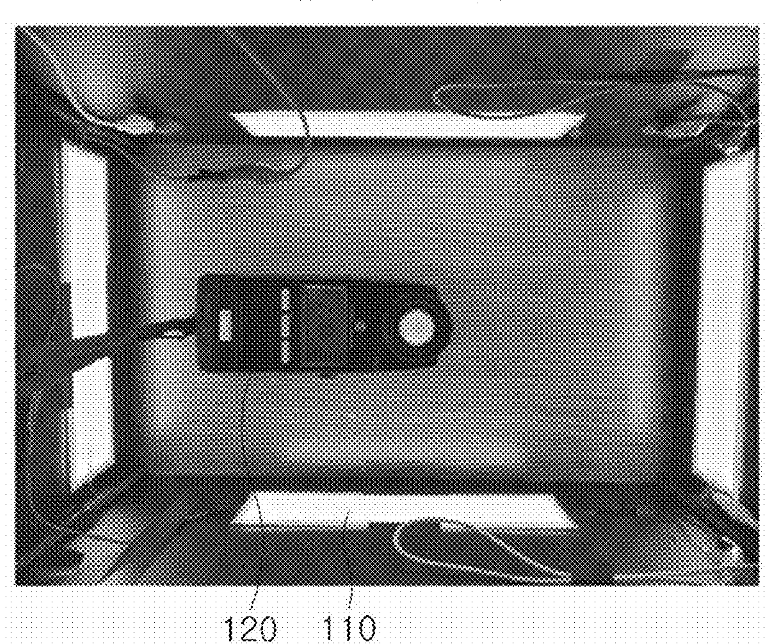
FIG. 6 is a view illustrating a device for performing a verification experiment on rats by realizing the visual stimulation platform of the present disclosure in a box form.

FIG. 6 is a view illustrating a device for performing a verification experiment on rats by realizing the visual stimulation platform 100 of the present disclosure in a box form.

As shown in FIG. 6, the Y-maze test and the NOR test were conducted to determine whether short-term visual stimulation by the OLED module 110 has an effect on improving cognitive ability in a condition that the OLED module 110 is installed on each lateral side wall of a hexahedral space where a mouse may enter, a device for the control unit 120 is realized, and a mouse is placed in an inner space.

Figure 7:
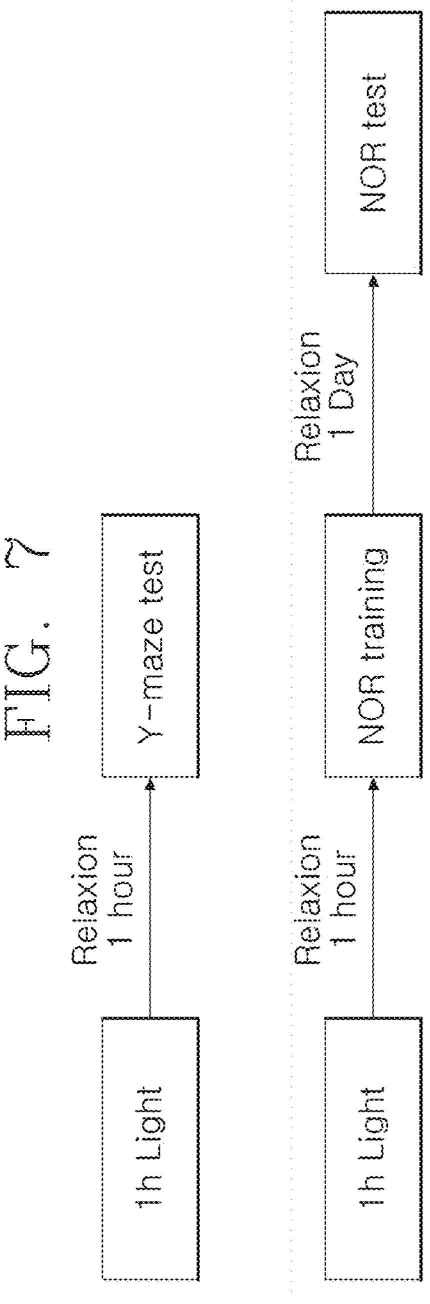
FIG. 7 is a view illustrating an experimental condition of a Y-maze test and a NOR test.

FIG. 7 is a view illustrating an experimental condition of a Y-maze test and a NOR test.

As shown in FIG. 7, the Y-maze test was conducted by repeating 1 hour of light emission by the OLED module 110 and 1 hour of rest time, and the NOR test was conducted by training after 1 hour of light emission by the OLED module 110, and testing after one day of rest.

For example, short-term visual stimulation was applied for 1 hour to an about 12-week-old 5XFAD dementia model mouse, using the experimental device as shown in FIG. 6. After 1 hour of rest, the Y-maze test, which measures short-term memory, and the novel object recognition (NOR) test, which measures long-term memory, were conducted, showing significant cognitive recovery effects as follows.

Figure 8:
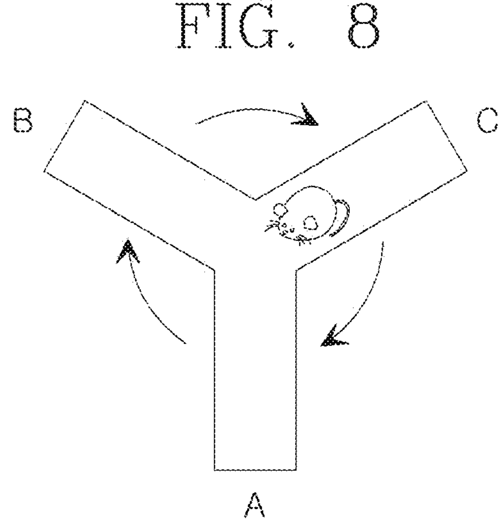
FIG. 8 is a graph depicting a result (alternation triplet) of a Y-maze test.
Figure 8:
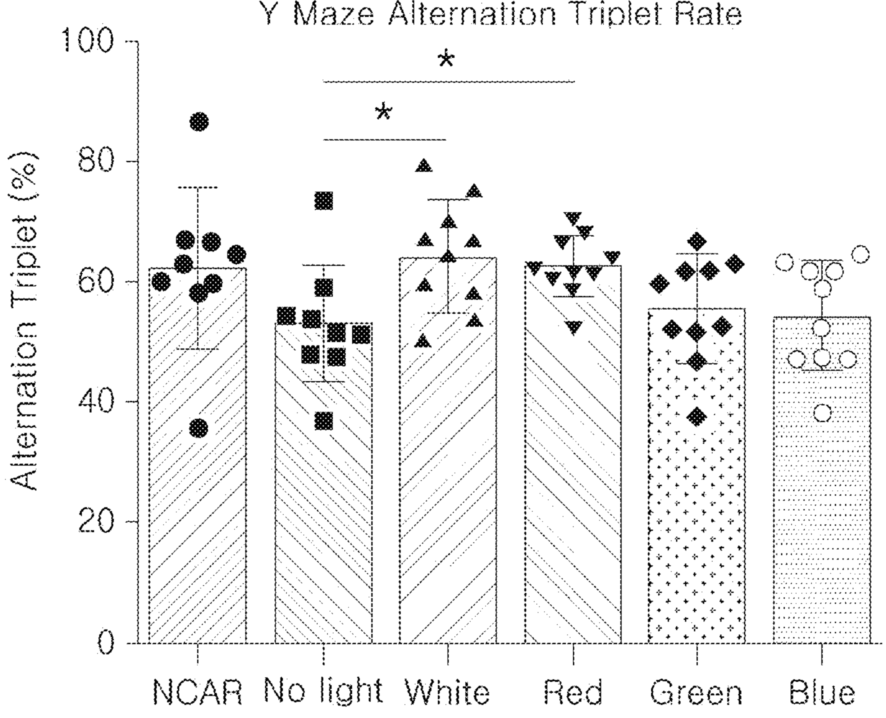

FIG. 8 is a graph depicting a result (alternation triplet) of a Y-maze test.

Figure 9:
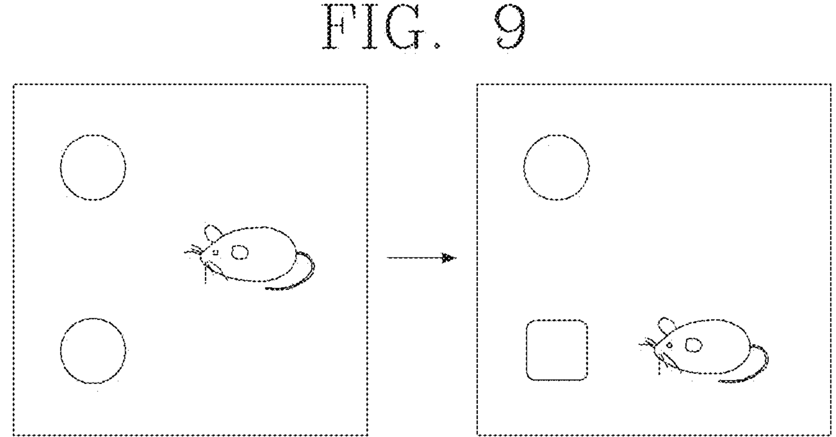
FIG. 9 is a graph depicting a result (discrimination rate) of a NOR test.
Figure 9:
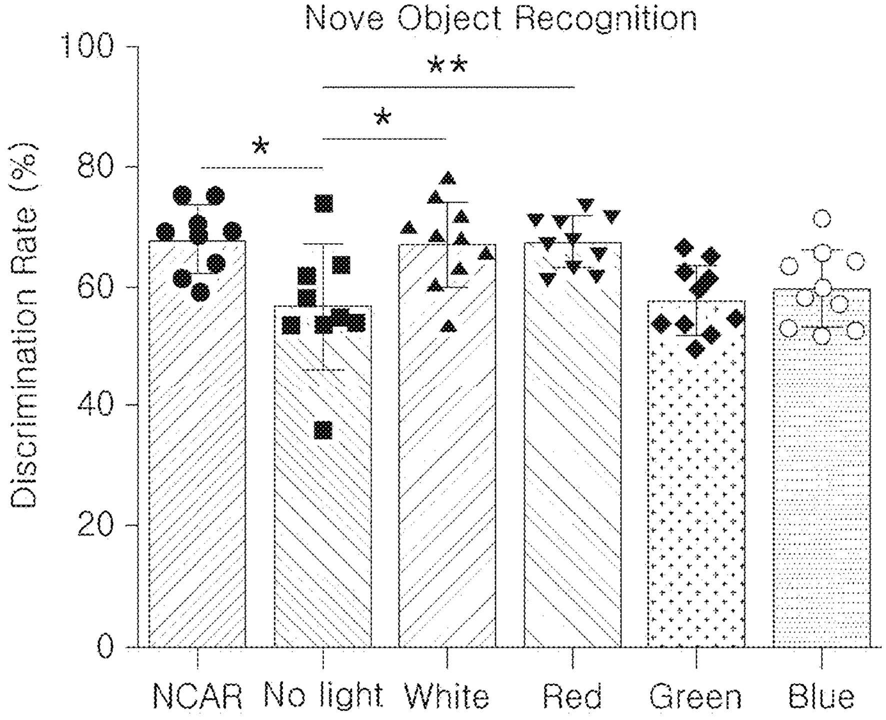

FIG. 9 is a graph depicting a result (discrimination rate) of a NOR test.

As shown in FIGS. 8 and 9, the tests on the dementia model mouse showed significant results indicating that, compared to the no visual stimulation (no-light) condition, when short-term visual stimulation at wavelengths such as white, red, green, and blue from the OLED module 110 according to the present disclosure is applied, cognitive abilities related to short-term and long-term memory were significantly restored to levels close to those of a normal mouse model (NCAR).

Furthermore, in a test to determine whether visual stimulation through the visual stimulation platform 100 of the present disclosure results in a reduction of amyloid beta within brain cells, which is known to be a cause of dementia, the following results were obtained.

Figure 11:
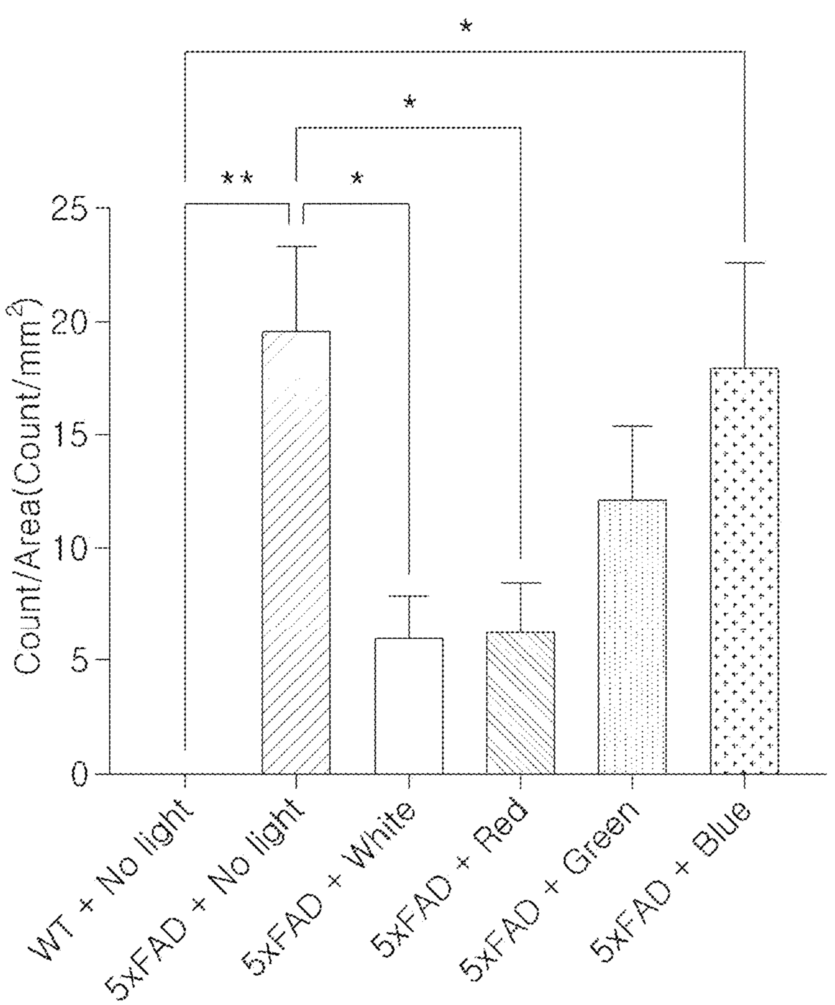
FIG. 11 is a graph depicting an experimental result for an effect of reducing accumulation of amyloid beta in rats in a 5XFAD dementia model according to visual stimulation for each wavelength through the visual stimulation platform 100 of the present disclosure.

FIG. 11 is a graph depicting an experimental result for an effect of reducing accumulation of amyloid beta in rats in a 5XFAD dementia model according to visual stimulation for each wavelength through the visual stimulation platform 100 of the present disclosure. Here, the illuminance (brightness) for each color during the test was W (white) 1067 lux, R (red) 228 lux, G (green) 249 lux, and B (blue) 199 lux. In the drawing, WT (wild type) is a normal mouse, and even when there is no light stimulation (no light), there is no amyloid beta accumulated in brain cells.

As shown in the drawing, it may be identified that the decrease in the accumulation of amyloid beta is clear in the W (white) and R (red) wavelength ranges, and the decrease in the accumulation of amyloid beta to a certain extent also appears in the G (green) wavelength range. In addition, it may be identified that although W (white) and R (red) showed a 5-fold difference in illuminance, there is no significant difference in amyloid beta reduction and consequent cognitive improvement effect (see FIG. 9). Therefore, it may be seen that it is advantageous for the treatment effect to select the R (red) wavelength range rather than W (white) if the same illuminance is configured.

Therefore, it is desirable to control the OLED module 110 to generate light in the W (white), R (red), or G (green) wavelength range through the wavelength setting unit 125 in the visual stimulation platform 100 of the present disclosure.

However, the illuminance is set through the brightness setting unit 122, so that a better treatment effect may be achieved in the same wavelength range, but the maximum allowable illuminance is limited to a maximum of 3000 lux in Korea depending on the purpose (KS A 3011, Korean Industrial Standard illuminance standards). Therefore, it is impossible to increase an illumination level indefinitely for the treatment effect, and the R (red) wavelength range is advantageous for the maximum treatment effect, and it is necessary to configure the appropriate illumination intensity within the maximum allowable intensity as described above depending on the purpose. In addition, since W (white) includes a B (blue) wavelength, there may be concerns in terms of safety in that fatigue and macular degeneration may be caused by blue light during visual stimulation at a short distance for treatment, and thus the R (red) wavelength range is advantageous in this regard as well.

As such, it has been identified that the use of the present disclosure may effectively help restore cognitive ability even with short-term visual stimulation for symptoms of mild cognitive impairment or dementia. In addition, with respect to light treatment of other neurological diseases such as sleep disorder, it is possible to achieve a treatment effect by using light stimulation of various colors. Furthermore, even when applied to a user having normal cognitive abilities, a function of preventing dementia may be achieved by reducing amyloid beta. As such, the present disclosure may help prevent and treat neurological diseases such as sleep disorders, dementia, and Alzheimer's on the basis of short-term uniform visual stimulation anytime and anywhere.

Furthermore, the visual stimulation platform 100 of the present disclosure may operate in two modes. That is, the visual stimulation platform 100 of the present disclosure may operate in a first mode for stimulating the eyes of the user with light generated from the OLED module 110 and in a second mode in which the (eye) field of view of the user wearing the visual stimulation platform 100 is secured through the OLED module 110 when the light generation of the OLED module 110 is turned off. This is possible by a combination configuration of the brightness setting unit 122 and the duty ratio setting unit 124. It is also possible that the first mode or the second mode is selected from a predetermined menu through the user interface.

The second mode is designed for a case in which a patient is performing daily activities, necessary tasks, or work in addition to receiving treatment, depending on a treatment situation, and it is intended to allow the patient to receive treatment effects through visual stimulation through the visual stimulation platform 100 without interference from activities other than treatment. The anode electrode 112 and the cathode electrode 114 of the OLED module 110 include a semi-permeable film or a transparent conductive film as described above, and thus it may be realized by securing the (eye) field of view of the user wearing the visual stimulation platform 100 through the OLED module 110.

For example, when operating in one of the first mode and the second mode, with respect to the operating time set through the time setting unit 121, it is preferably to configure the second mode to have a larger value (time) than the first mode. Since only visual stimulation is performed in the first mode, and the duty ratio of frequency driving of light generation on/off is small in the second mode as described below, in order for the overall time of visual stimulation to be at the same level, such configuration may be required depending on situations.

Figure 12:
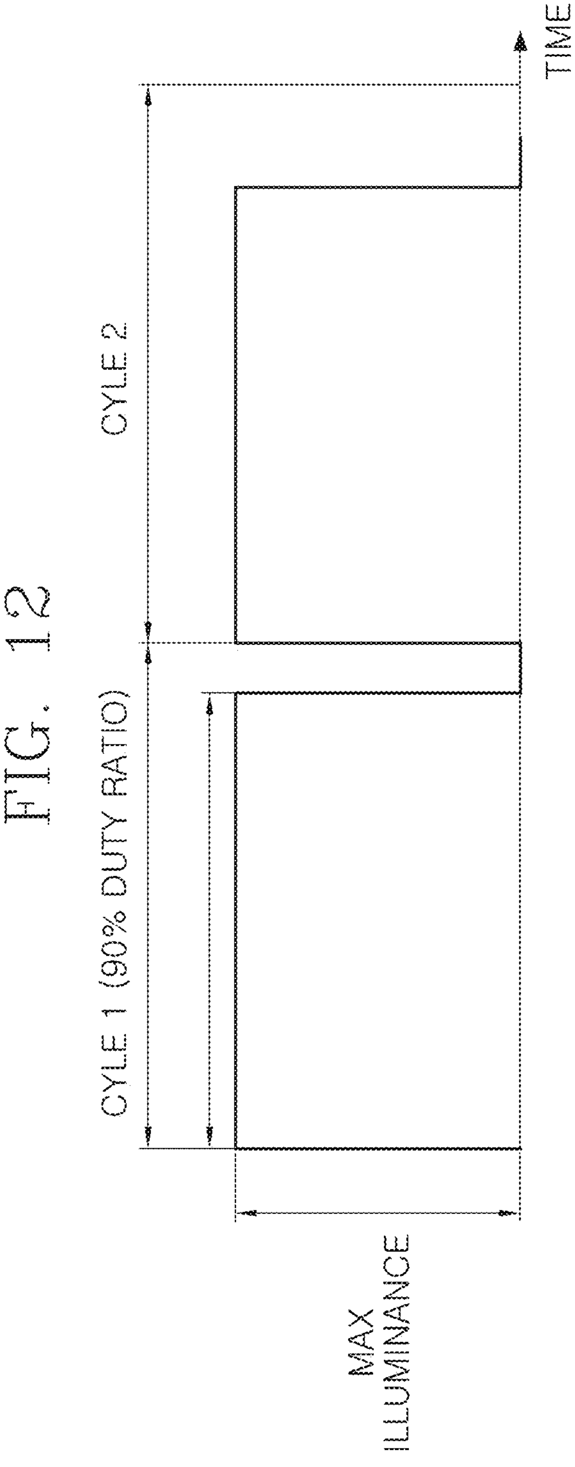
FIG. 12 is a view illustrating setting of a duty ratio of illumination and light generation on/off in a first mode of the visual stimulation platform 100 of the present disclosure.

FIG. 12 is a view illustrating setting of a duty ratio of illumination and light generation on/off in a first mode of the visual stimulation platform 100 of the present disclosure.

Referring to FIG. 12, for example, through voltage/current control in a form of a square wave signal with respect to the OLED module 110 as shown in FIG. 12, a maximum value of the square wave signal may be configured to have a maximum illuminance of 500 to 1000 lux while the OLED module 110 is turned on. Here, the duty ratio may be appropriately configured regardless of the user's field of view, and is preferably configured to 70% or more, and 90% is most preferable. As described above, light in the W (white), R (red), or G (green) wavelength range is preferably for the light generated by the OLED module 110, and light in R (red) wavelength range is most preferable.

Figure 13:
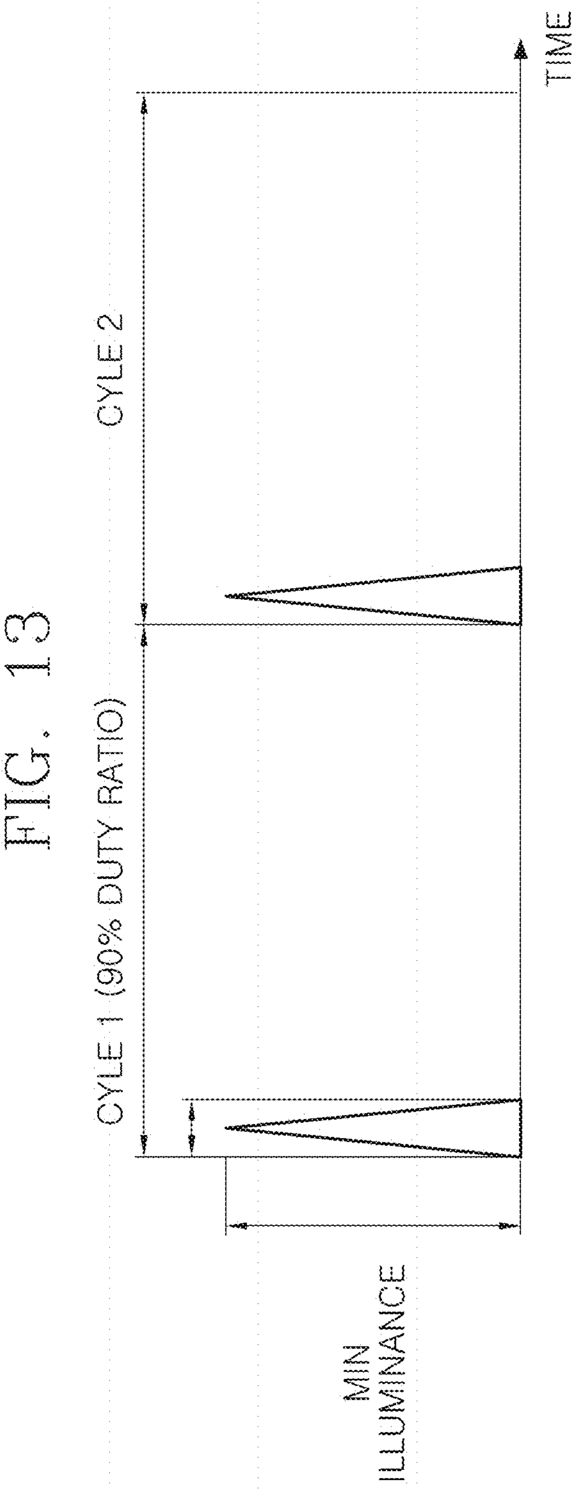
FIG. 13 is a view illustrating setting of a duty ratio of illumination and light generation on/off in a second mode of the visual stimulation platform 100 of the present disclosure.

FIG. 13 is a view illustrating setting of a duty ratio of illumination and light generation on/off in a second mode of the visual stimulation platform 100 of the present disclosure.

Referring to FIG. 13, for example, in order to correspond to a minimum illuminance to bring a visual stimulation effect while the OLED module 110 is turned on, through voltage/current control in a form of a triangular wave signal with respect to the OLED module 110 as shown in FIG. 13, a maximum value of the triangular wave signal may be configured to have a maximum illuminance of 10 to 50 lux. Here, the duty ratio may be set to secure the user's field of view, for example, it is preferable to be set in a range of 5 to 15%, and 10% is most preferable. As described above, light in the W (white), R (red), or G (green) wavelength range is preferably for the light generated by the OLED module 110, and light in R (red) wavelength range is most preferable.

Referring to FIGS. 12 and 13, for example, in the case of operating in the second mode, while frequency driving of light generation on/off set through the frequency setting unit 123 is performed, it is preferable to set brightness (illuminance) of light set by the brightness setting unit 122 to have a smaller value (illuminance) in the second mode than in the first mode while the OLED module 110 is turned on. In this case, it is preferable to set a duty ratio set through the duty ratio setting unit 124 at the same frequency set through the frequency setting unit 123 to have a smaller value (duty ratio) in the second mode than in the first mode.

As described above, according to the short-term visual stimulation platform 100 of the present disclosure, it is possible to uniformly emit light to a wide emission range by using a safe and convenient organic light source of an OLED so as to effectively prevent deterioration of cognitive ability and achieve quick recovery through behavioral modification with respect to visual stimulation for controlling a brain function of a subject with a brain lesion disorder, such as sleep disorders, dementia, and Alzheimer's disease, consume low power due to short-term visual stimulation, and significantly lower a side effect, such as possibility of tissue destruction due to local light stimulation so that effective visual stimulation may be achieved. Furthermore, multicolor organic light emission is possible through a frequency adjustment technology so that it is possible to provide a light wavelength optimized to achieve effective treatment for cognitive ability improvement and various neurological diseases such as a sleep disorder.

Furthermore, according to the short-term visual stimulation platform 100 of the present disclosure, it is possible to provide stable visual stimulation even to a moving subject by using a uniform and extensive light emission characteristic of the OLED through the visual stimulation platform (e.g., glasses) on which multicolor OLEDs are deposited, and provide a light wavelength optimized for a neurological disease requiring treatment by using a wavelength adjustment technology.

For example, according to the present disclosure, the use of OLED as a light source may enable uniform light emission with respect to a target visual stimulation range and selection of a wavelength optimized for non-invasive visual stimulation so as to obtain an effect in treatment for recovering a cognitive ability of the subject with a low power consumption of about 1 to 10 W even for short-term (e.g., about 1 hour) visual stimulation. In addition, according to the present disclosure, a light-emitting layer of the OLED, which is a light source, may configure a multicolor light emitting source by using white light, a color filter, a micro-cavity, patterning, and the like. Therefore, even within one visual stimulation platform, light having various wavelengths may be emitted and thus it is possible to select a customized light source wavelength not only for cognitive ability improvement but also for various neurological diseases, such as a sleep disorder. In addition, the OLED light source is advantageous in that the OLED light source has excellent flexibility and stretchability compared to other light sources, may be applied to various curved surfaces and materials, and thus may be unrestrictedly applied to various platforms, such as glasses, hats, augmented reality/virtual reality (AR/VR) devices, head-up displays (HUD), patches, hair bands, and lenses. In addition, stable visual stimulation is possible in that light reaching the eyeball may be designed to be uniform according to a curvature of a substrate.

As such, in the present disclosure, specific matters such as specific components, etc., and limited embodiments and drawings have been described, but these are only provided to help a more general understanding of the present disclosure, and the present disclosure is not limited to the above embodiments. Those of ordinary skill in the field to which the present disclosure pertains will be able to make various modifications and variations without departing from the essential characteristics of the present invention. Therefore, the spirit of the disclosure should not be limited to the above-described embodiments, and it should be construed that the following claims as well as all technical ideas modified equally or equivalently to the claims are intended to fall within the scope and spirit of the disclosure.

The invention claimed is:

1. A visual stimulation platform comprising:

an OLED module comprising an anode electrode and a cathode electrode which are made of a semi-permeable film or a transparent conductive film;

a controller configured to control an operation of the OLED module; and a power supply configured to supply operating power to the OLED module and the controller, wherein the visual stimulation platform is configured as a wearable device to project light generated from the OLED module to eyes of a user according to control of the controller, wherein the controller comprises a wavelength setter, a time setter, a brightness setter, a frequency setter, and a duty ratio setter for light generation of the OLED module, wherein the OLED module is configured to generate light in at least one wavelength range of W (white), R (red), or G (green) through the wavelength setter, wherein the controller is configured to control:

a first mode in which light generated from the OLED module stimulates the user's eye, and a second mode in which, when the light generation of the OLED module is turned off, a field of view of the user wearing the visual stimulation platform is secured through the OLED module, wherein in case of operating in one selected from among the first mode and the second mode, a time set through the time setter has a greater value in the second mode than in the first mode to ensure an equivalent level of visual stimulation in both modes, and wherein in case of operating in the second mode, while a light generation on and off frequency driving set through the frequency setter is performed to simultaneously enable visual stimulation and field of view securing:

a brightness of light during a turn-on period of the OLED module set through the brightness setter has a smaller value in the second mode than in the first mode, and at an identical frequency set through the frequency setter, a duty ratio set through the duty ratio setter has a smaller value in the second mode than in the first mode.

2. The visual stimulation platform of claim 1, wherein the OLED module comprises a white light OLED panel and a color filter configured to transmit light of a specific wavelength range, or emits light of a wavelength range according to an EML design thereof without a color filter.

3. The visual stimulation platform of claim 1, wherein the OLED module adopts a micro-cavity method that emits light of a specific wavelength range.

4. The visual stimulation platform of claim 1, wherein the OLED module comprises multiple OLED areas having different emission colors, and wherein the wavelength setter is configured to control one or more of the multiple OLED areas to be selectively operated and generate corresponding light.

5. The visual stimulation platform of claim 4, wherein the multiple OLED areas comprise one white light OLED panel and a color filter configured to transmit light of different wavelength ranges, or comprise areas configured to emit light of different wavelength ranges according to an EML design thereof without a color filter.

6. The visual stimulation platform of claim 1, wherein the time setter is configured to control light generation in a range of 30 minutes to 2 hours, wherein the brightness setter is configured to control light generation in a range of 10 to 1000 lux, wherein the frequency setter is configured to control continuous light generation driving or light generation on and off frequency driving of 1 to 100 Hz, and wherein the duty ratio setter is configured to control a duty ratio of 10 to 90% of the frequency driving.

7. The visual stimulation platform of claim 1, wherein the visual stimulation platform corresponds to a wearable item configured to be close to the user's eyes and enable the visual stimulation when worn by the user.

8. The visual stimulation platform of claim 7, wherein the wearable item comprises glasses, a patch, or a lens.

9. The visual stimulation platform of claim 1, wherein the visual stimulation platform is additionally provided on a wearable product so as to configure a wearable item to be close to the user's eyes and enable the visual stimulation when worn by the user.

10. The visual stimulation platform of claim 9, wherein the wearable product comprises an AR/VR device comprising a hat, a hair band, or a head-up display (HUD).

* * * * *